United States Patent

Takeda et al.

[11] Patent Number: 4,665,068
[45] Date of Patent: May 12, 1987

[54] NOVEL 9-CHLORO-1,5-BENZOTHIAZEPINE DERIVATIVES AND THEIR PHARMACEUTICAL USE

[75] Inventors: Mikio Takeda, Urawa; Tokuro Oh-ishi, Tokyo; Hiromichi Nakajima, Urawa; Taku Nagao, Tokyo, all of Japan

[73] Assignee: Tanabe Seiyaku Co., Ltd., Japan

[21] Appl. No.: 793,628

[22] Filed: Oct. 31, 1985

[30] Foreign Application Priority Data

Nov. 17, 1984 [GB] United Kingdom ................ 8429102

[51] Int. Cl.[4] ..................... A61K 31/55; C07D 281/10
[52] U.S. Cl. ..................................... 514/211; 540/491
[58] Field of Search ................ 260/239.3 B; 514/211; 540/491

[56] References Cited

U.S. PATENT DOCUMENTS

| | | | |
|---|---|---|---|
| 3,075,967 | 1/1963 | Krapcho et al. | 540/491 |
| 3,341,519 | 9/1967 | Krapcho et al. | 540/491 |
| 3,562,257 | 2/1971 | Kugita et al. | 260/239.3 B |
| 4,585,768 | 4/1986 | Takeda et al. | 260/239 |

FOREIGN PATENT DOCUMENTS 296070 1/1970 United Kingdom ................ 540/491

*Primary Examiner*—Robert T. Bond
*Attorney, Agent, or Firm*—Scully, Scott, Murphy & Presser

[57] ABSTRACT

Novel 1,5-benzothiazepine derivative of the formula:

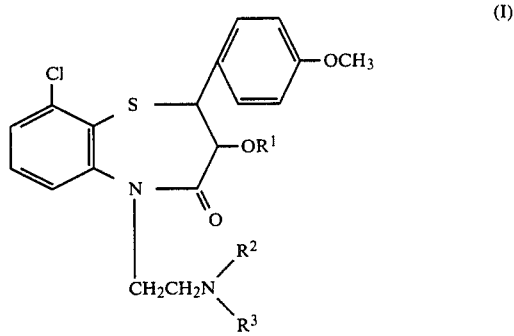

wherein $R^1$ is hydrogen or lower alkanoyl and each of $R^2$ and $R^3$ is lower alkyl, and a pharmaceutically acceptable acid addition salt thereof are disclosed.

Said derivative (I) and a salt thereof are useful as a hypotensive agent and/or a cerebral or coronary vasodilator.

14 Claims, No Drawings

NOVEL 9-CHLORO-1,5-BENZOTHIAZEPINE DERIVATIVES AND THEIR PHARMACEUTICAL USE

This invention relates to novel 9-chloro-1,5-benzothiazepine derivatives and processes for preparing the same. More particularly, it relates to a compound of the formula:

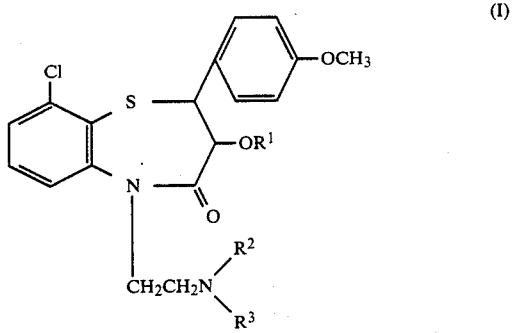

wherein $R^1$ is hydrogen or lower alkanoyl and each of $R^2$ and $R^3$ is lower alkyl, or a pharmaceutically acceptable acid addition salt thereof.

U.S. Pat. No. 3,562,257 discloses various benzothiazepine derivatives including 7-chloro-1,5-benzothiazepine derivatives such as 2-(4-methoxyphenyl)-3-hydroxy (or acetoxy)-5-[2-(dimethylamino)ethyl]-7-chloro-2,3-dihydro-1,5-benzothiazepin-4(5H)-one. Said U.S. patent also discloses that these benzothiazepine derivatives show antidepressive, tranquilizing and/or coronary vasodilating activities.

As a result of various investigations, we have now found that the compound (I) of the present invention or a pharmaceutically acceptable acid addition salt thereof is useful as a hypotensive agent and/or a cerebral or coronary vasodilator. The compound (I) of the invention is especially characteristic in that it shows a potent hypotensive activity. For example, when administered orally to spontaneously hypertensive rats (SHR), (+)-cis-2-(4-methoxyphenyl)-3-acetoxy-5-[2-(dimethylamino)ethyl]-9-chloro-2,3-dihydro-1,5-benzothiazepin-4(5H)-one hydrochloride at a dose of 30 mg/kg shows a decrease of about 74 mm Hg or 54 mm Hg in blood pressure of said SHR one or 4 hours after administration of the test compound.

The compound (I) of the present invention also shows a potent cerebral or coronary vasodilating activity. For example, (+)-cis-2-(4-methoxyphenyl)-3-acetoxy-5-[2-(dimethylamino)ethyl]-9-chloro-2,3-dihydro-1,5-benzothiazepin-4(5H)-one hydrochloride and (+)-cis-2-(4-methoxyphenyl)-3-hydroxy-5-[2-(dimethylamino)ethyl]-9-chloro-2,3-dihydro-1,5-benzothiazepin-4(5H)-one perchlorate when administered intraarterially to anesthetized dogs show remarkable increase in vertebral artery blood flow, and said cerebral vasodilating activity of the compounds of the invention is about 15 to 22 times stronger than that of papaverine and more than 3 times stronger than that of (±)-cis-2-(4-methoxyphenyl)-3-acetoxy-5-[2-(dimethylamino)ethyl]-7-chloro-2,3-dihydro-1,5-benzothiazepin-4(5H)-one hydrochloride. On the other hand, when the coronary vasodilating activity is estimated by the Langendorff method using isolated hearts of guinea pigs, said activity of (+)-cis-2-(4-methoxyphenyl)-3-acetoxy-5-[2-(dimethylamino)ethyl]-9-chloro-2,3-dihydro-1,5-benzothiazepin-4(5H)-one hydrochloride is about 10 times stronger than that of papaverine.

Moreover, the compound (I) of the present invention is characterized by its longer-lasting therapeutic effects (i.e., longer-lasting hypotensive activity and longer-lasting cerebral or coronary vasodilating activity) as compared with (±)-cis-2-(4-methoxyphenyl)-3-acetoxy-5-[2-(dimethylamino)ethyl]-7-chloro-2,3-dihydro-1,5-benzothiazepin-4(5H)-one.

In addition, the compound (I) of the present invention has a potent platelet aggregation-inhibiting activity, shows no substantial side effects (e.g., central nervous system effect) and, at the same time, is low in toxicity. For example, the acute toxicity ($LD_{50}$) of (+)-cis-2-(4-methoxypnenyl)-3-acetoxy-5-[2-(dimethylamino)ethyl]-9-chloro-2,3-dihydro-1,5-benzothiazepin-4(5H)-one hydrochloride when orally administered to mice is about 1,000 mg/kg.

Representative examples of the compounds of the present invention include those of the formula (I) in which $R^1$ is hydrogen or lower alkanoyl of 2 to 5 carbon atoms such as acetyl, propionyl, butyryl or valeryl; and each of $R^2$ and $R^3$ is lower alkyl of one to 4 carbon atoms such as methyl, ethyl, propyl or butyl. Among the compounds of the present invention, a preferred subgenus is those of the formula (I) in which $R^1$ is hydrogen or acetyl, and each of $R^2$ and $R^3$ is methyl.

While the compound (I) of the present invention can exist in the form of two stereoisomers (i.e., cis and trans isomers) or four optical isomers (i.e., (+)-cis, (−)-cis, (+)-trans and (−)-trans isomers) due to the two asymmetric carbon atoms involved therein, all of these optical isomers or a mixture thereof are included within the scope of the invention. Among said isomers, however, the cis isomer, especially the (+)-cis isomers, of the compound (I) is preferred for medicinal use.

According to the present invention, the compound (I) can be prepared by condensing a compound of the formula:

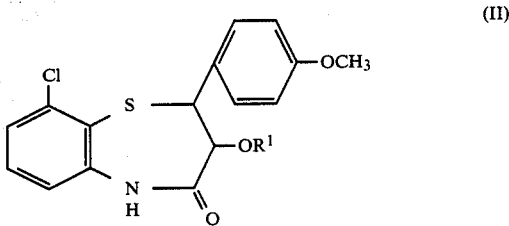

wherein $R^1$ is the same as defined above, or a salt thereof with a compound of the formula:

wherein $R^2$ and $R^3$ are the same as defined above and X is halogen, or a salt thereof.

Alternatively, the compound (I) in which $R^1$ is lower alkanoyl may be prepared by acylating a compound of the formula:

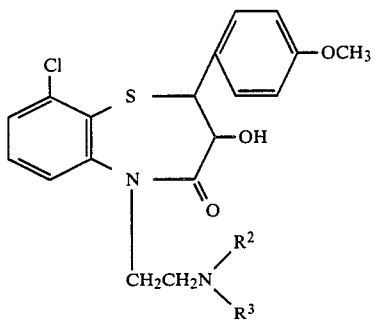

(I-a)

wherein R² and R³ are the same as defined above, or a salt thereof with a lower alkanoic acid of the formula:

R⁴COOH (IV)

wherein R⁴ is lower alkyl, or a reactive derivative thereof.

The condensation of the compound (II) or a salt thereof with the compound (III) or a salt thereof can be carried out in a solvent. Suitable salt of the compound (II) includes, for example, alkali metal salts such as sodium or potassium salts. When the compound (II) is used in free form, it is preferred to carry out the reaction in the presence of an alkali agent. The alkali agent includes, for example, alkali metal hydroxide (e.g. potassium hydroxide, sodium hydroxide), alkali metal carbonate (e.g., potassium carbonate, sodium carbonate) and alkali metal hydride (e.g., sodium hydride). Examples of the salt of the compound (III) includes acid addition salts thereof such as hydrochloride, hydrobromide and so forth. Acetone, ethyl acetate, dimethylsulfoxide, dimethylformamide, acetonitrile, tetrahydrofuran, dioxane, aqueous acetone and aqueous ethyl acetate are suitable as the solvent. It is preferred to carry out the reaction at a temperature of 0° to 100° C., especially at 20° to 70° C.

The acylation of the compound (I-a) or a salt thereof with the reactive derivative of the lower alkanolic acid (IV) can be conducted in a solvent in the presence or absence of an acid acceptor. Examples of the salt of the compound (I-a) include acid addition salts thereof such as hydrochloride, hydrobromide and so forth. The reactive derivative of the lower alkanolic acid (IV) includes, for example, lower alknaolic acid anhydride (e.g., acetic anhydride, propionic anhydride) and lower alkanoyl halide (e.g., acetyl chloride, propionyl chloride, butyryl chloride, valeryl chloride). The acid acceptor includes, for example, pyridine, triethylamine, N-methylpiperidine, N-methylmorpholine, N-methylpyrrolidine and N-ethyl-N,N-diisopropylamine. Acetic acid, chloroform, dichloromethane, dimethylformamide and tetrahydrofuran are suitable as the solvent. When an excess amount of acetic anhydride is used as the reactive derivative of the lower alkanoic acid (IV), it is not always necessary to use the solvent because said acetic anhydride serves as the solvent. It is preferred to carry out the reaction at a temperature of −10° to 140° C.; e.g., at a temperature of 20° to 140° C. if the lower alkanoic acid anhydride is used as the reactive derivative of the lower alkanoic acid (IV); or at a temperature of −10° to 100° C. if the lower alkanoic acid halide is used as the reactive derivative.

On the other hand, the acylation of the compound (I-a) or a salt thereof with the lower alkanoic acid (IV) may be carried out in a solvent in the presence of a condensing agent. The condensing agent includes, for example, dicyclohexylcarbodiimide, N,N'-carbonyldiimidazole, 1-methyl-2-halopyridinium iodide (e.g., 1-methyl-2-bromopyridinium iodide), methoxyacetylene and (C₆H₅)₃P-CCl₄. Methylene chloride, 1,2-dichloroethane, chloroform, benzene, toluene, tetrahydrofuran and dioxane are suitable as the solvent. It is preferred to carry out the reaction at a temperature of 0° to 50° C., especially at 0° to 25° C.

The starting compound (II) of the present invention involves four optical isomers due to the two asymmetric carbon atoms at the 2- and 3-positions of benzothiazepine skeleton. Since all of the above-mentioned reactions of the invention can be carried out without racemization, the compound (I) of the invention in an optically active form can be readily obtained from the corresponding optically active isomer of the compound (II) or (I-a).

The starting compound (II) is novel and can be prepared by the step(s) of:

(A) (a) reacting 2-amino-6-chlorothiophenol (V) with a glycidic ester of the formula:

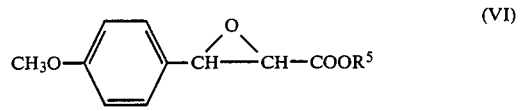

(VI)

wherein R⁵ is lower alkyl, to give a compound of the formula:

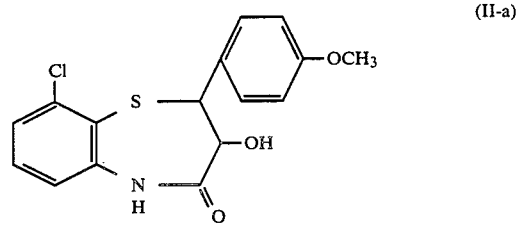

(II-a)

or (b) subjecting a propionic acid compound of the formula:

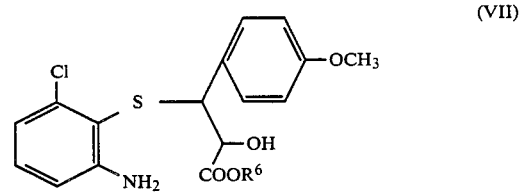

(VII)

wherein R⁶ is hydrogen or lower alkyl, to intramolecular cyclization to give the compound (II-a), and (B) if required, further acylating the compound (II-a) with a lower alkanoic acid of the formula:

R⁴COOH (IV)

wherein R⁴ is the same as defined above, or a reactive derivative thereof to give a compound of the formula:

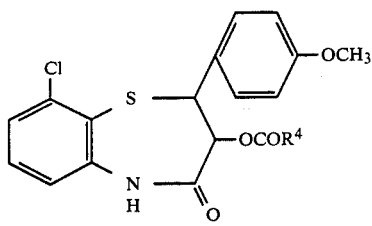

(II-b)

wherein R⁴ is the same as defined above.

The reaction of the 2-amino-6-chlorothiophenol (V) with the glycidic ester (VI) may be accomplished by heating a mixture of these compounds at a temperature of 130° to 180° C. The reaction may be carried out either in a solvent (e.g., xylene, diphenyl ether or p-cymene) or without solvent. When the reaction product thus obtained is a mixture of the compound (II-a) and the propionic acid compound (VII) (R⁶=lower alkyl) or a mixture of two stereoisomers (i.e., cis and trans isomers) of the compound (II-a), they may be separated from each other by their difference in solubility in a solvent such as lower alkanol (e.g., ethanol) and/or by column chromatography.

The intramolecular cyclization of the propionic acid compound (VII) can be carried out by heating it either in a solvent or without solvent. Xylene, toluene, diphenyl ether, p-cymene and acetic acid are suitable as the solvent. It is preferred to carry out the reaction at a temperature of 110° to 160° C., especially under refluxing. Alternatively, the intramolecular cyclization of the propionic acid compound (VII) (R⁶=lower alkyl) may be carried out at 0° to 30° C. in the presence of methylsulfinylcarbanion (CH₃SOCH₂⁻) (prepared from dimethylsulfoxide and sodium hydride) in a solvent (e.g., dimethylsulfoxide). Moreover, the intramolecular cyclization of the propionic acid compound (VII) (R⁶=hydrogen) may be carried out in the presence of a condensing agent. Dicyclohexylcarbodiimide is used alone as the condensing agent or in combination with 1-hydroxybenzotriazole, 4-dimethylaminopyridine, N-hydroxyphthalimide, N-hydroxysuccinimide, trichlorophenol, p-nitrophenol or 3-hydroxy-4-oxo-3,4-dihydro-1,2,3,-benzotriazine. Carbonyldiimidazole, ethoxyacetylene and 1-methyl-2-halopyridinium halide (e.g., 1-methyl-2-chloropyridinium iodide or 1-methyl-2-bromopyridinium iodide) are also used as the condensing agent. 1-Methyl-2-halopyridinium halide, the condensing agent, may be used in combination with a base such as triethylamine or tributylamine. Chloroform, dimethylformamide, carbon tetrachloride, dichloromethane, 1,2-dichloroethane, ethyl acetate, and dioxane are suitable as the solvent. It is preferred to carry out the reaction at a temperature of −10° to 70° C.

If required, the racemic modification of the compound (II-a) thus-obtained may be resolved into each optical enantiomers thereof by using an optically active 1-(2-naphthylsulfonyl)pyrrolidine-2-carbonyl chloride as a resolving agent, for example, by the steps of reacting the compound (II-a) with (S)-1-(2-naphthylsulfonyl)pyrrolidine-2-carbonyl chloride to give a pair of diastereoisomers, separating said diastereoisomers from each other by selective crystallization or column chromatography, and then hydrolysing each of diastereoisomers to give the optically active compound (II-a). When a mixture of the optically active compound (II-a) and the optically active compound (VII) (R⁶=H) is produced by the hydrolysis of the diastereoisomer, they may be separated from each other by taking advantage of the difference in solubilities thereof.

The subsequent optional acylaton of the compound (II-a) with the lower alkanoic acid (IV) or a reactive derivative thereof can be carried out under the same conditions as employed in acylation of the compound (I-a).

The starting compound (VII) used in the above mentioned reaction can be prepared, for example, according to the methods described in Japanese Patent Publication (examined) Nos. 9383/1970, 8982/1971, 36221/1974 or 24954/1975, or Japanese Patent Publication (unexamined) Nos. 142963/1982, 176951/1982 or 193449/1982.

The compound (I) of the invention can be used for pharmaceutical use either as the free base or as a pharmaceutically acceptable acid addition salt thereof. Pharmaceutically acceptable acid addition salts of the compound (I) are, for example, inorganic acid addition salts such as hydrochloride, hydrobromide, hydroiodide, perchlorate, sulfate or phosphate, or organic acid addition salts such as oxalate, maleate, fumarate, tartrate or methanesulfonate, and so forth. These salts may be prepared, for example, by neutralizing the compound (I) with an acid. The compound (I) or a pharmaceutically acceptable acid addition salt thereof can be administered either orally or parenterally. Further, the compound (I) or a salt thereof may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills, capsules or suppositories; or in liquid form such as solutions, suspensions or emulsions. Further, when administered parenterally, the pharmaceutical preparation may be used in the form of injections.

As mentioned hereinbefore, the compound (I) of the present invention has a potent hypotensive activity, a potent cerebral or coronary vasodilating activity, and a potent platelet aggregation-inhibiting activity. Therefore, the compound (I) is useful for the treatment, amelioration or prophylaxis of hypertension; cerebral diseases such as cerebral vasospasm or cerebral infarction; and heart diseases such as angina pectoris, arrhythmias or coronary or cardiac infarction in a warm-blooded animal including human being. Especially, since the compound (I) of the present invention shows stronger and longer-lasting therapeutic effects (i.e., hypotensive, cerebral and coronary vasodilating activities) as compared with the 7-chloro-derivative (e.g., (±)-cis-2-(4-methoxyphenyl)-3-acetoxy-5-[2-(dimethylamino)ethyl]-7-chloro-2,3-dihydro-1,5-benzothiazepin-4(5H)-one) of U.S. Pat. No. 3,562,257, the compound (I) of the present invention is much more useful as a hypotensive agent or a cerebral or coronary vasodilator than the above-mentioned 7-chloro-derivative. Therapeutic dose of the compound (I) or a salt thereof may vary depending on route of administration, the age, weight and conditions of patients; and particular diseases to be treated. In general, however, it may be used at a dose of 0.05 to 10 mg/kg/day, especially at a dose of 0.5 to 10 mg/kg/day in the case of oral administration or at a dose of 0.05 to 2 mg/kg/day in the case of parenteral administration (e.g., intravenous injection).

Practically and presently preferred embodiments of the present invention are illustratively shown in the following lines. Throughout the specification and claims, the terms "lower alkyl", "lower alkanoyl" and "lower alkanoic acid" should be interpreted as referring to straight or branched alkyl of one to 4 carbon atoms, straight or branched alkanoyl of 2 to 5 carbon atoms and straight or branched alkanoic acid of 2 to 5 carbon atoms, respectively.

Concomitantly, throughout the specification and claims, the term "threo" means that the hydroxy and 2-amino-6-chlorophenylthio (or 2-chloro-6-nitrophenylthio) groups substituted at the 2- and 3-positions of propionic acid have threo-type configuration (i.e., said two groups are placed on opposite side of the central bond in the Fisher's projection formula).

EXPERIMENT 1

(Hypotensive activity)

A test compound (dose: 30 mg/kg) dissolved or suspended in water was administered orally to spontaneously hypertensive rats (SHR) (one group: 3 rats) fasted overnight. The systolic blood pressure of the rats was measured by the tail plethysmographic technique (The Journal of Laboratory and Clinical Medicine 78(1971), page 957). The hypotensive activity of the test compound was estimated at one or 4 hours after dosing and expressed as "−" if the decrease in blood pressure is less than 10 mm Hg; "+" if the decrease is not less than 10 mm Hg but less than 20 mm Hg; "++" if the decrease is not less than 20 mm Hg but less than 40 mm Hg; "+++" if the decrease is not less than 40 mm Hg but less than 60 mm Hg; or "++++" if the decrease is not less than 60 mm Hg.

The results are shown in the following Table 1.

TABLE 1

| Test compounds | Hypotensive activity A period of time after dosing | |
|---|---|---|
|  | 1 hr | 4 hrs |
| (The compounds of the present invention) | | |
| (±)-cis-2-(4-methoxyphenyl)-3-acetoxy-5-[2-(dimethylamino)ethyl]-9-chloro-2,3-dihydro-1,5-benzothiazepin-4(5H)—one hydrochloride | +++ | +++ |
| (+)-cis-2-(4-methoxyphenyl)-3-hydroxy-5-[2-(dimethylamino)ethyl]-9-chloro-2,3-dihydro-1,5-benzothiazepin-4(5H)—one perchlorate | +++ | ++ |
| (+)-cis-2-(4-methoxyphenyl)-3-acetoxy-5-[2-(dimethylamino)ethyl]-9-chloro-2,3-dihydro-1,5-benzothiazepin-4(5H)—one hydrochloride (known compound) | ++++ | +++ |
| (+)-cis-2-(4-methoxyphenyl)-3-acetoxy-5-[2-(dimethylamino)ethyl]-7-chloro-2,3-dihydro-1,5-benzothiazepin-4(5H)—one hydrochloride | ++ | + |

EXPERIMENT 2

(Cerebral vasodilating activity)

Male dogs weighing 10 to 20 kg were anesthetized with sodium pentobarbital (30 mg/kg, intravenous injection). The blood flow in vertebral artery was measured continuously by means of an electromagnetic flowmeter under artificial respiration. A test compound dissolved in an aqueous 5% glucose solution was injected into vertebral artery. The cerebral vasodilating activity of the test compound was estimated in terms of the potency ratio of said compound to papaverine, which was calculated from the dose-response curves thereof.

The results are shown in the following Table 2.

TABLE 2

| Test compounds | Cerebral vasodilating activity (potency ratio) |
|---|---|
| (The compounds of the present invention) | |
| (+)-cis-2-(4-methoxyphenyl)-3-hydroxy-5-[2-(dimethylamino)ethyl]-9-chloro-2,3-dihydro-1,5-benzothiazepin-4(5H)—one perchlorate | 22 |
| (+)-cis-2-(4-methoxyphenyl)-3-acetoxy-5-[2-(dimethylamino)ethyl]-9-chloro-2,3-dihydro-1,5-benzothiazepin-4(5H)—one hydrochloride | 15 |
| (Known compound) | |
| (±)-cis-2-(4-methoxyphenyl)-3-acetoxy-5-[2-(dimethylamino)ethyl]-7-chloro-2,3-dihydro-1,5-benzothiazepin-4(5H)—one hydrochloride (Positive control) | 5 |
| Papaverine | 1 |

EXPERIMENT 3

(Coronary vasodilating activity)

Langendorff's method was used for testing the effect on the coronary blood flow of the isolated heart of guinea pig (about 280 g). The isolated heart was perfused with Locke-Ringer solution containing 2% of defibrinated rabbit blood, which had been saturated with a mixed gas of 95% $O_2$ and 5% $CO_2$ (30° C.). Perfusion pressure was kept at 40 cm $H_2O$. A solution of a test compound in an aqueous 5% glucose solution was injected into the perfusing solution at a volume of 0.1 ml per heart. The outflow of the perfusate was measured by means of a drop counter.

The coronary vasodilating activity of the test compound was expressed as "±" if the increase in coronary blood flow is less than 0.5 ml/minute at a dose of 100 μg/heart; "+" if the increase is not less than 0.5 ml/minute at a dose of 100 μg/heart; "++" if the increase is not less than 0.5 ml/minute at a dose of 30 μg/heart; and "+++" if the increase is not less than 0.5 ml/minute at a dose of not more than 10 μg/heart.

The results are shown in the following Table 3.

TABLE 3

| Test compounds | Coronary vasodilating activity |
|---|---|
| (The compounds of the present invention) | |
| (±)-cis-2-(4-methoxyphenyl)-3-hydroxy-5-[2-(dimethylamino)ethyl]-9-chloro-2,3-dihydro-1,5-benzothiazepin-4(5H)—one hydrochloride | +++ |
| (±)-cis-2-(4-methoxyphenyl)-3-acetoxy-5-[2-(dimethylamino)ethyl]-9-chloro-2,3-dihydro-1,5-benzothiazepin-4(5H)—one hydrochloride | +++ |
| (+)-cis-2-(4-methoxyphenyl)-3-hydroxy-5-[2-(dimethylamino)ethyl]-9-chloro-2,3-dihydro-1,5-benzothiazepin-4(5H)—one perchlorate | +++ |
| (+)-cis-2-(4-methoxyphenyl)-3-acetoxy-5-[2-(dimethylamino)ethyl]-9-chloro-2,3-dihydro-1,5-benzothiazepin-4(5H)—one hydrochloride | +++ |
| (Positive control) | |
| Papaverine | + |

EXPERIMENT 4

(Platelet aggregation-inhibiting activity)

Blood was collected from the abdominal aorta of male Sprague-Dawley rats which were anesthetized with ether. Nine volumes of rat blood were mixed with one volume of an aqueous trisodium citrate solution, and the mixture was centrifuged to give platelet-rich plasma ("PRP") as the supernatant solution. The bottom layer was further centrifuged to give platelet-poor plasma ("PPP") as the supernatant solution. Platelet counts were adjusted to $0.8-1\times10^6/mm^3$ for PRP by dilution with PPP. After a mixture of 200 μl of the diluted PRP and 25 μl of a test compound solution (final concentration: 100 μg/ml) was stirred for 2 minutes at 37° C., 25 μl of a collagen solution [Biochim. Biophys. Acta, 186, page 254(1969)] were added thereto. The degree of platelet aggregation was estimated by Born's method [Nature, 194, page 927(1962)] and the percentage inhibition of platelet aggregation was calculated therefrom. The platelet aggregation-inhibiting activity of the test compound was expressed as (−) if the test compound showed less than 10% inhibition of platelet aggregation; (+) if the test compound showed not less than 10% inhibition of platelet aggregation but said percentage inhibition was lower than that of acetylsalicylic acid (100 μg/ml); or (++) if the test compound showed the platelet aggregation-inhibiting activity at least as strong as that of acetylsalicylic acid (100 μg/ml).

The results are shown in the following Table 4.

TABLE 4

| Test compounds | Platelet aggregation-inhibiting activity |
| --- | --- |
| (The compounds of the present invention) | |
| (±)-cis-2-(4-methoxyphenyl)-3-hydroxy-5-[2-(dimethylamino)ethyl]-9-chloro-2,3-dihydro-1,5-benzothiazepin-4(5H)—one hydrochloride | ++ |
| (±)-cis-2-(4-methoxyphenyl)-3-acetoxy-5-[2-(dimethylamino)ethyl]-9-chloro-2,3-dihydro-1,5-benzothiazepin-4(5H)—one hydrochloride | ++ |

EXAMPLE 1

A mixture of 2.01 g of (±)-cis-2-(4-methoxyphenyl)-3-hydroxy-9-chloro-2,3-dihydro-1,5-benzothiazepin-4(5H)-one, 0.95 g of 2-(dimethylamino)ethyl chloride hydrochloride, 2.49 g of powdered potassium carbonate, 60 ml of acetone and 0.6 ml of water is refluxed for 23 hours. After the reaction is completed, insoluble materials are removed by filtration. The filtrate is evaporated to remove solvent. The residue is digested with isopropyl ether and the resultant crystals are collected by filtration and recrystallized from ethyl acetate. 1.84 g of (±)-cis-2-(4-methoxypheny)-3-hydroxy-5-[2-(dimethylamino)ethyl]-9-chloro-2,3-dihydro-1,5-benzothiazepin-4(5H)-one are obtained. Yield: 75.4%

M.p. 143°–144° C.

Hydrochloride hydrate:

M.p. 228°–230° C. (decomp.) (turbid melt at 143° C.) (recrystallized from methanol)

EXAMPLE 2

A mixture of 0.95 g of (±)-cis-2-(4-methoxyphenyl)-3-hydroxy-5-[2-(dimethylamino)ethyl]-9-chloro-2,3-dihydro-1,5-benzothiazepin-4(5H)-one hydrochloride hydrate, 10 ml of acetic anhydride and 10 ml of acetic acid is stirred at 110° C. for 6.5 hours. After the reaction is completed, the reaction mixture is evaporated under reduced pressure to remove solvent. Toluene is added to the residue, and the mixture is evaporated under reduced pressure to remove solvent. The residue is recrystallized from a mixture of methanol and ether. 0.93 g of (±)-cis-2-(4-methoxyphenyl)-3-acetoxy-5-[2-(dimethylamino)ethyl]-9-chloro-2,3-dihydro-1,5-benzothiazepin-4(5H)-one hydrochloride hydrate is obtained. Yield: 89.4%

M.p. 185°–189° C. (turbid melt at at about 150° C.)

EXAMPLE 3

A mixture of 4.00 gof optically active cis-2-(4-methoxyphenyl)-3-hydroxy-9-chloro-2,3-dihydro-1,5-benzothiazepin-4(5H)-one (the lactum A obtained in Preparation 3-(2-a)), 1.80 g of 2-(dimethylamino)ethyl chloride hydrochloride, 5.7 g of powdered potassium carbonate and 150 ml of acetone is refluxed for 20 hours. After the reaction is completed, insoluble materials are removed by filtration. The filtrate is evaporated to remove solvent. The residue is converted to its perchlorate and recrystallized from methanol. 4.63 g of (+)-cis-2-(4-methoxyphenyl)-3-hydroxy-5-[2-(dimethylamino)ethyl]-9-chloro-2,3-dihydro-1,5-benzothiazepin-4(5H)-one perchlorate ¼ hydrate are obtained. Yield: 76.0%

M.p. 190°–192° C.

$[\alpha]_D^{20}+10.2°$ (C=0.334, dimethylformamide)

EXAMPLE 4

A mixture of 2.84 g of (+)-cis-2-(4-methoxyphenyl)-3-hydroxy-5-[2-(dimethylamino)ethyl]-9-chloro-2,3-dihydro-1,5-benzothiazepin-4(5H)-one, 30 ml of acetic anhydride and 30 drops of pyridine is stirred at 100° C. for 4 hours. After the reaction is completed, the reaction mixture is evaporated under reduced pressure to remove solvent. Toluene is added to the residue, and the mixture is evaporated under reduced pressure to remove solvent. The residue is converted to its hydrochloride and recrystallized from a mixture of ethanol and ether. 3.02 g of (+)-cis-2-(4-methoxyphenyl)-3-acetoxy-5-[2-(dimethylamino)ethyl]-9-chloro-2,3-dihydro-1,5-benzothiazepin-4(5H)-one hydrochloride hydrate are obtained.

Yield: 85.9%

M.p. 140°–143° C.

$[\alpha]_D^{20}+13.0°$ (C=0.347, methanol)

EXAMPLE 5

A mixture of 2.00 g of optically active cis-2-(4-methoxyphenyl)-3-hydroxy-9-chloro-2,3-dihydro-1,5-benzothiazepin-4(5H)-one (the lactam B obtained in Preparation 3-(2-b)), 0.90 g of 2-(dimethylamino)ethyl chloride hydrochloride, 2.89 g of powdered potassium carbonate and 100 ml of acetone is treated in the same manner as described in Example 3. 2.68 g of (−)-cis-2-(4-methoxyphenyl)-3-hydroxy-5-[2-(dimethylamino)ethyl]-9-chloro-2,3-dihydro-1,5-benzothiazepin-4(5H)-one perchlorate ¼ hydrate are obtained. Yield: 87.9%

M.p. 190°–192° C.

$[\alpha]_D^{20}-10.3°$ (C=0.321 dimethylformamide)

EXAMPLE 6

A mixture of 1.27 g of (−)-cis-2-(4-methoxyphenyl)-3-hydroxy-5-[2-(dimethylamino)ethyl]-9-chloro-2,3-dihydro-1,5-benzothiazepin-4-(5H)-one, 15 ml of acetic anhydride and 15 drops of pyridine is treated in the same manner as described in Example 4. 1.40 g of (−)-cis-2-(4-methoxyphenyl)-3-acetoxy-5-[2-(dimethylamino)ethyl]-9-chloro-2,3-dihydro-1,5-benzothiazepin-4(5H)-one hydrochloride hydrate are obtained.

Yield: 88.9%
M.p. 139°–142° C.
$[\alpha]_D^2 -13.0°$ (C=0.348, methanol)

EXAMPLE 7

A mixture of 200 mg of (±)-cis-2-(4-methoxyphenyl)-3-acetoxy-9-chloro-2,3-dihydro-1,5-benzothiazepin-4(5H)-one, 84 mg of 2-(dimethylamino)ethyl chloride hydrochloride, 220 mg of powdered potassium carbonate and 10 ml of acetone is refluxed for 20 hours. After the reaction is completed, insoluble materials are removed by filtration. The filtrate is evaporated to remove solvent. The residue is converted to its hydrochloride and then recrystallized from methanol. 226 mg of (±)-cis-2-(4-methoxyphenyl)-3-acetoxy-5-[2-(dimethylamino)ethyl]-9-chloro-2,3-dihydro-1,5-benzothiazepin-4(5H)-one hydrochloride hydrate are obtained.
Yield: 85%

The physico-chemical properties of the product are identical with the product obtained in Example 2.

PREPARATION OF STARTING COMPOUND

Preparation 1

(1) A mixture of 40.58 g of 2-chloro-6-nitrothiophenol, 60.15 g of methyl trans-3-(4-methoxyphenyl)-glycidate, 1 g of zinc acetate dihydrate and 410 ml of toluene is stirred at room temperature for 3 hours under argon atmosphere. The reaction mixture is evaporated under reduced pressure to remove toluene. Isopropyl ether is added to the residue and the precipitated crystals are collected by filtration. The crystals are recrystallized from a mixture of ethyl acetate and hexane (the filtrate is hereinafter referred to as "mother liquor I"). 62.37 g of methyl threo-2-hydroxy-3-(2-chloro-6-nitrophenylthio)-3-(4-methoxyphenyl)propionate are obtained.

M.p. 110°–111.5° C.

The mother liquor I is subjected to silica gel chromatography (Solvent: benzene-ethyl acetate (20:1)), whereby 2.93 g of methyl threo-2-hydroxy-3-(2-chloro-6-nitrophenylthio)-3-(4-methoxyphenyl)propionate are further obtained.

M.p. 109.5°–111° C.

(2) A mixture of 62 g of methyl threo-2-hydroxy-3-(2-chloro-6-nitrophenylthio)-3-(4-methoxyphenyl)propionate, 7 g of 10% palladium-charcoal, 500 ml of acetic acid and 500 ml of ethanol is shaken at room temperature in hydrogen gas atmosphere for 11 hours under an atmospheric pressure. Insoluble materials are removed by filtration. The filtrate is evaporated under reduced pressure to remove solvent and the residue is recrystallized from a mixture of ethyl acetate and hexane. 51.74 g of methyl threo-2-hydroxy-3-(2-amino-6-chlorophenylthio)-3-(4-methoxyphenyl)propionate are obtained.

M.p. 114°–116° C.

(3) 84 mg of sodium hydride (60% oil dispersion) are added to 2 ml of dimethylsulfoxide, and the mixture is stirred at 70° C. for 40 minutes under argon atmosphere. After cooling the mixture, a solution of 0.368 g of methyl threo-2-hydroxy-3-(2-amino-6-chlorophenylthio)-3-(4-methoxyphenyl)propionate in 1 ml of dimethylsulfoxide is added thereto, and the mixture is stirred at room temperature for 40 minutes. Then, the reaction mixture is poured into a mixture of ice and acetic acid and the precipitated crystals are collected by filtration. Said crystals are washed with water, dried and recrystallized from a mixture of chloroform and ethanol. 0.163 g of (±)-cis-2-(4-methoxyphenyl)-3-hydroxy-9-chloro-2,3-dihydro-1,5-benzothiazepin-4(5H)-one is obtained.

M.p. 249°–252° C. (decomp.)

Preparation 2

(1) A mixture of 18.39 g of methyl threo-2-hydroxy-3-(2-amino-6-chlorophenylthio)-3-(4-methoxyphenyl)-propionate, 90 ml of 10% sodium hydroxide, 200 ml of methanol and 90 ml of water is stirred at room temperature for 4 hours. The reaction mixture is adjusted to a pH of about 2 under ice-cooling and is stirred at room temperature overnight. The precipitated crystals are collected by filtration, washed with water and dried. 16.77 g of threo-2-hydroxy-3-(2-amino-6-chlorophenylthio)-3-(4-methoxyphenyl)propionic acid hemihydrate are obtained.

M.p. 108°–110° C. (recrystallized from a mixture of ethanol and water)

(2) A mixture of 15.77 g of threo-2-hydroxy-3-(2-amino-6-chlorophenylthio)-3-(4-methoxyphenyl)propionic acid hemihydrate and 630 ml of xylene is refluxed for 18 hours while removing the resulting water by a dehydration apparatus. After cooling the reaction mixture, the precipitated crystals are collected by filtration. 10.44 g of (±)-cis-2-(4-methoxyphenyl)-3-hydroxy-9-chloro-2,3-dihydro-1,5-benzothiazepin-4(5H)-one are obtained.

M.p. 249°–251° C. (decomp.)

When the product is recrystallized from a mixture of dimethylformamide and isopropyl ether, said product shows m.p. 247°–250° C. (decomp.)

Preparation 3

(1) A mixture of 22.39 g of (±)-cis-2-(4-methoxyphenyl)-3-hydroxy-9-chloro-2,3-dihydro-1,5-benzothiazepin-4(5H)-one, 60 ml of pyridine is cooled with ice-water, and 28.4 g of (S)-1-(2-naphthylsulfonyl)pyrrolidine-2-carbonyl chloride (prepared from (S)-1-(2-naphthylsulfonyl)pyrrolidine-2-carboxylic acid and oxalyl chloride in anhydrous benzene) are added thereto. The mixture is stirred at room temperature for 18 hours. Water and a mixture of ethyl acetate and chloroform (1:1) are added to the reaction mixture. The organic layer is collected therefrom and washed with 10% hydrochloric acid, water, an aqueous 5% sodium bicarbonate solution and water, successively. The solution is dried and then evaporated. The residue is chromatographed on silica gel (Solvent: benzene-ethyl acetate (9:1)), whereby 18.22 g of the product "A" (oil, $[\alpha]_D^{20} -113.2°$ (C=0.326, chloroform)) and 17.01 g of the product "B" (crystalline product, M.p. 106°–123° C., $[\alpha]_D^{20} +22.8°$ (C=0.324, chloroform)) are obtained.

(2-a) A mixture of 17.46 g of the product "A" obtained in paragraph (1), 41 g of potassium carbonate, 100 ml of water and 200 ml of methanol is stirred at room temperature for 19 hours. After the reaction, the precipitated crystals (needles) are collected by filtration and recrystallized from aqueous methanol. 7.85 g of optically active cis-2-(4-methoxyphenyl)-3-hydroxy-9-chloro-2,3-dihydro-1,5-benzothiazepin-4(5H)-one (this product is referred to as "lactam A") are obtained. Yield: 83.4%

M.p. 188°–189° C.

$[\alpha]_D^{20}$ 0° (C=0.275, dimethylfomamide)

(2-b) A mixture of 12.75 g of the product B obtained in paragraph (1), 30 g of potassium carbonate, 75 ml of water and 150 ml of methanol is stirred at room temperature for 20 hours. After the reaction, the precipitated crystals (needles) are collected by filtration and recrystallized from aqueous methanol. 6.01 g of optically active cis-2-(4-methoxyphenyl)-3-hydroxy-9-chloro-2,3-dihydro-1,5-benzothiazepin-4(5H)-one (this product is referred to as "lactam B") are obtained. Yield: 91.3%

M.p. 188°–189° C.

$[\alpha]_D^{20}$ 0° (C=0.477, dimethylformamide)

Preparation 4

A mixture of 2.27 g of the product "B" obtained in Preparation 3-(1), 40 ml of an aqueous 5% sodium hydroxide solution and 40 ml of methanol is stirred at room temperature for 18 hours. After the reaction is completed, the mixture is diluted with water and then extracted with chloroform. The extract is washed with water, dried and evaporated to remove solvent. The residue is recrystallized from aqueous methanol, whereby 287 mg of optically active cis-2-(4-methoxyphenyl)-3-hydroxy-9-chloro-2,3-dihydro-1,5-benzothiazepin-4(5H)-one (lactam B) are obtained.

On the other hand, the aqueous layer is adjusted to pH 3–4 with 10% hydrochloric acid and then extracted with chloroform. The extract is washed with water, dried and evaporated to remove solvent. The residue (oil, 1.7 g) is dissolved in benzene-ether, and then extracted with conc.-hydrochloric acid. The hydrochloric acid layer is adjusted to pH 4 with potassium carbonate and then extracted with chloroform. The extract is washed with water, dried and evaporated to remove solvent. 640 mg of (—)-threo-2-hydroxy-3-(2-amino-6-chlorophenylthio)-3-(4-methoxyphenyl)propionic acid are obtained as an oil.

$[\alpha]_D^{20}$ −158° (C=0.520, chloroform)

Preparation 5

600 mg of (—)-threo-2-hydroxy-3-(2-amino-6-chlorophenylthio)-3-(4-methoxyphenyl)propionic acid are dissolved in a mixture of 2 ml of dimethylformamide and 5 ml of dichloromethane. 150 mg of 1-hydroxybenzotriazole and 550 mg of dicyclohexylcarbodiimide are added to the solution. Then, the recipitated dicyclohexylurea (270 mg) is removed by filtration, and the filtrate is evaporated under reduced pressure to remove solvent. The residue is dissolved in ethyl acetate, and the solution is washed with an aqueous 5% sodium bicarbonate solution and water, successively. The washed solution is dried and evaporated to remove ethyl acetate. The residue is recrystallized from aqueous methanol. 414 mg of optically active cis-2-(4-methoxyphenyl)-3-hydroxy-9-chloro-2,3-dihydro-1,5-benzothiazepin-4(5H)-one (lactam B) are obtained.

Yield: 72.6%

M.p. 188°–189° C.

Preparation 6

220 mg of (±)-cis-2-(4-methoxyphenyl)-3-hydroxy-9-chloro-2,3-dihydro-1,5-benzothiazepin-4(5H)-one are dissolved in 1.5 ml of pyridine, and 61 mg of acetyl chloride are added thereto under ice-cooling. The mixture is stirred at room temperature for one hour. The reaction mixture is evaporated under reduced pressure to remove solvent. The residue is dissolved in ethyl acetate, and the solution is washed with 10% hydrochloric acid, water an aqueous 5% sodium bicarbonate solution and water, successively. The washed solution is dried and evaporated to remove solvent. The residue is recrystallized from ethyl acetate, whereby 206 mg of (±)-cis-2-(4-methoxyphenyl)-3-acetoxy-9-chloro-2,3-dihydro-1,5-benzothiazepin-4(5H)-one are obtained. Yield: 83.4%

M.p. 217°–219° C.

What we claim is:

1. A 1,5-benzothiazepine derivative of the formula:

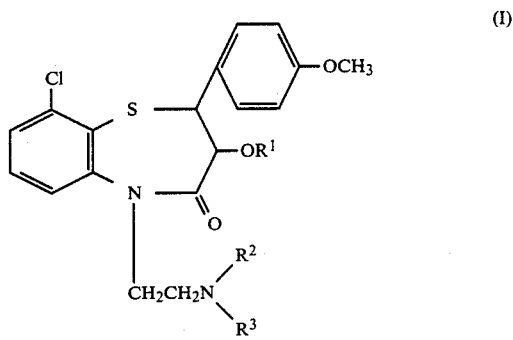

(I)

wherein $R^1$ is hydrogen or lower alkanoyl and each of $R^2$ and $R^3$ is lower alkyl, or a pharmaceutically acceptable acid addition salt thereof.

2. The compound according to claim 1, in which $R^1$ is hydrogen or alkanoyl to 2 to 5 carbon atoms and each of $R^2$ and $R^3$ is alkyl of 1 to 4 carbon atoms.

3. The compound according to claim 2, in which $R^1$ is hydrogen or acetyl, and $R^2$ and $R^3$ are methyl.

4. A cis isomer of the compound claimed in claim 1.

5. A cis isomer of the compound claimed in claim 2.

6. A cis isomer of the compound claimed in claim 3.

7. A (+)-cis isomer of the compound claimed in claim 1.

8. A (+)-cis isomer of the compound claimed in claim 2.

9. A (+)-cis isomer of the compound claimed in claim 3.

10. The compound of claim 9, which is (+)-cis-2-(4-methoxyphenyl)-3-hydroxy-5-[2-(dimethylamino)ethyl]-9-chloro-2,3-dihydro-1,5-benzothiazepin-4(5H)-one or a pharmaceutically acceptable acid addition salt thereof.

11. The compound of claim 9, which is (+)-cis-2-(4-methoxyphenyl)-3-acetoxy-5-[2-(dimethylamino)ethyl]-9-chloro-2,3-dihydro-1,5-benzothiazepin-4(5H)-one or a pharmaceutically acceptable acid addition salt thereof.

12. A 1,5-benzothiazepine derivative of the formula:

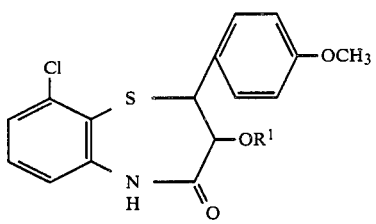

wherein R[1] is hydrogen or lower alkanoyl, or a salt thereof.

13. A pharmaceutical composition possessing a hypotensive, cerebral vasodilating and/or coronary vasodilating activity which comprises a therapeutically effective amount of a compound of claim 1, 3 or 9 and a pharmaceutically acceptablle carrier therefor.

14. A method of producing a hypotensive, cerebral vasodilating and/or coronary vasodilating effect on a warm-blooded animal comprising administering to said warm-blooded animal an effective amount of the compound claimed in claim 1, 3 or 9.

* * * * *